US011266668B2

(12) United States Patent
Wu et al.

(10) Patent No.: US 11,266,668 B2
(45) Date of Patent: *Mar. 8, 2022

(54) DIETARY SUPPLEMENT FOR GLYCEMIA CONTROL AND DIABETES PREVENTION

(71) Applicant: WORLD PHARMACEUTICAL TECHNOLOGY, LLC., Rowland Heights, CA (US)

(72) Inventors: Yong Wu, Downey, CA (US); Wei Cao, Downey, CA (US); Jieqing Li, Downey, CA (US); Huabing Yang, Wuhan (CN); Ke Wu, Wuhan (CN); Shiliu Tian, Shanghai (CN)

(73) Assignee: WORLD PHARMACEUTICAL TECHNOLOGY, LLC, Rowland Heights, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/792,109

(22) Filed: Feb. 14, 2020

(65) Prior Publication Data

US 2020/0197429 A1 Jun. 25, 2020

Related U.S. Application Data

(63) Continuation-in-part of application No. 16/231,200, filed on Dec. 21, 2018, now Pat. No. 10,757,961.

(51) Int. Cl.
| | |
|---|---|
| *A61K 31/7034* | (2006.01) |
| *A61K 36/605* | (2006.01) |
| *A61K 36/63* | (2006.01) |
| *A61K 36/42* | (2006.01) |
| *A61P 3/10* | (2006.01) |
| *A61K 31/375* | (2006.01) |
| *A61K 33/24* | (2019.01) |
| *A61K 31/593* | (2006.01) |
| *A61K 9/00* | (2006.01) |
| *A61K 31/4188* | (2006.01) |

(52) U.S. Cl.
CPC ........ *A61K 31/7034* (2013.01); *A61K 9/0053* (2013.01); *A61K 31/375* (2013.01); *A61K 31/4188* (2013.01); *A61K 31/593* (2013.01); *A61K 33/24* (2013.01); *A61K 36/42* (2013.01); *A61K 36/605* (2013.01); *A61K 36/63* (2013.01); *A61P 3/10* (2018.01)

(58) Field of Classification Search
None
See application file for complete search history.

(56) References Cited

U.S. PATENT DOCUMENTS

| | | |
|---|---|---|
| 6,692,777 B2 | 2/2004 | Lee |
| 6,852,760 B1 | 2/2005 | Fine et al. |
| 8,679,550 B2 | 3/2014 | West et al. |
| 10,757,961 B2 * | 9/2020 | Wu .......................... A61K 9/10 |
| 2008/0306011 A1 | 12/2008 | Tokuda et al. |
| 2016/0004298 A1 | 1/2016 | Mazed et al. |

OTHER PUBLICATIONS

Zhen-Yuan Zhu, et al., Comparative evaluation of polysaccharides isolated from *Astragalus*, oyster mushroom, and yacon as inhibitors of α-glucosidase, Chinese Journal of Natural Medicines, 2014, pp. 290-293, vol./Issue 12(4), Elsevier, China.

Yong Wu, et al., Hypoglycemic effect of Astragalus polysaccharide and its effect on PTP1B[1], Acta Pharmacologica Sinica, Mar. 2005, pp. 345-352, vol./Issue 26(3), Blackwell Publishing, China.

B. Jiang, et al., Abstract: Astragaloside IV attenuates lipolysis and improves insulin resistance induced by TNFalpha in 3T3-L1 adipocytes, Phytother Res., Nov. 2008, 2 Pages, vol./Issue 22(11), John Wiley & Sons, Inc., U.S. Website: https://www.ncbi.nlm.nih.gov/pubmed/?term=Astragaloside+IV+attenuates+lipolysis+and+improves+insulin+resistance+induced+by+TNFalpha+in+3T3-L1+adipocytes.

Herbert Chasis, et al., The Action of Phlorizin on the Excretion of Glucose, Xylose, Sucrose, Creatinine and Urea by Man, The Journal of Clinical Investigation, 1933, pp. 1083-1090, vol./Issue 12(6), American Society for Clinical Investigation, U.S.

K. Miyamoto, et al., Abstract: Diabetes and glucose transporter gene expression in rat small intestine, Biochem Biophys Res Commun., Dec. 31, 1991, 2 Pages, vol./Issue 181(3), Elsevier, U.S. Website: https://www.ncbi.nlm.nih.gov/pubmed/1722397.

Hidetada Ogata, et al., $K_{ATP}$ channel as well as SGLT1 participates in GIP secretion in the diabetic state, Journal of Endocrinology, Society for Endocrinology, 2014, pp. 191-200, vol./Issue 222:2, Bioscientifica Ltd., Great Britain.

R. Grempler, et al., Empagliflozin, a novel selective sodium glucose cotransporter-2 (SGLT-2) inhibitor: characterisation and comparison with other SGLT-2 inhibitors, Diabetes Obes Metab., Jan. 2012, 2 Pages, vol./Issue 14(1), Blackwell Publishing Ltd., U.S. Website: https://www.ncbi.nlm.nih.gov/pubmed/21985634.

Y. Fujita, et al., Increased intestinal glucose absorption and postprandial hyperglycaemia at the early step of glucose intolerance in Otsuka Long-Evans Tokushima Fatty Rats, Diabetologia, 1998, pp. 1459-1466, vol. 41, Springer-Verlag, Japan.

Robert L. Dobbins, et al., Selective sodium-dependent glucose transporter 1 inhibitors block glucose absorption and impair glucose-dependent insulinotropic peptide release, Am J Physiol Gastrointest Liver Physiol, Mar. 12, 2015, pp. G946-G954, vol. 308, The American Physiological Society, U.S.

Valentin Gorboulev, et al., Na$^+$-$_D$-glucose Cotransporter SGLT1 is Pivotal for Intestinal Glucose Absorption and Glucose-Dependent Incretin Secretion, Diabetes, Jan. 2012, pp. 187-196, vol. 61, The American Diabetes Association, U.S.

(Continued)

*Primary Examiner* — Susan Hoffman

(74) *Attorney, Agent, or Firm* — Lewis Roca Rothgerber Christie LLP

(57) ABSTRACT

A formulation for a dietary supplement includes standardized extracts of *astragalus* root, phlorizin, root bark of white mulberry, olive leaf, and bitter melon. The formulation may further include chromium, 2-deoxy-D-glucose, biotin, vitamin D and vitamin C. A method of controlling postprandial blood glucose includes administering the formulation for the dietary supplement to a patient.

16 Claims, 3 Drawing Sheets

(56) References Cited

OTHER PUBLICATIONS

Volker Vallon, et al., SGLT2 Mediates Glucose Reabsorption in the Early Proximal Tubule, J Am Soc Nephrol, 2011, pp. 104-112, vol. 22, The American Society of Nephrology, U.S.
Timo Rieg, et al., Increase in SGLT1-mediated transport explains renal glucose reabsorption during genetic and pharmacological SGLT2 inhibition in euglycemia, Am J Physiol Renal Physiol, Nov. 13, 2013, pp. F188-F193, vol. 306, American Physiological Society, U.S.
Volker Vallon, et al., Knockout of Na-glucose transporter SGLT2 attenuates hyperglycemia and glomerular hyperfiltration but not kidney growth or injury in diabetes mellitus, Am J Physiol Renal Physiol, Nov. 14, 2012, pp. F156-F167, vol. 304, American Physiological Society, U.S.
Volker Vallon, et al., SGLT2 inhibitor empagliflozin reduces renal growth and albuminuria in proportion to hyperglycemia and prevents glomerular hyperfiltration in diabetic Akita mice, Am J Physiol Renal Physiol, Nov. 13, 2013, pp. F194-F204, vol. 306, American Physiological Society, U.S.
Xiaoxin X. Wang, et al., A dual agonist of farnesoid X receptor (FXR) and the G protein-coupled receptor TGR5, INT-767, reverses age-related kidney disease in mice, JBC Accelerated Communication, 2017, pp. 12018-12024, vol./Issue 292(29), Journal of Biological Chemistry, American Society for Biochemistry and Molecular Biology, U.S.
Luciano Rossetti, et al., Correction of hyperglycemia with phlorizin normalizes tissue sensitivity to insulin in diabetic rats, JCI The Journal of Clinical Investigation, 1987, pp. 1510-1515, vol./Issue 79(5), The American Society for Clinical Investigation, Inc., U.S.
Luciano Rossetti, et al., Effect of chronic hyperglycemia on in vivo insulin secretion in partially pancreatectomized rats, JCI The Journal of Clinical Investigation, 1987, pp. 1037-1044, vol./Issue 80(4), The American Society for Clinical Investigation, Inc., U.S.
Rachel Dorothy Shannon, et al., Effects of white mulberry (*Morus alba*) leaf tea investigated in a type 2 diabetes model of rats, Acta Poloniae Pharmaceutica—Drug Research, 2015, pp. 153-160, vol. 72, Issue 1, Polish Pharmaceutical Society, Poland.
B. Andallu, et al., Abstract: Effect of mulberry (*Morus indica* L.) therapy on plasma and erythrocyte membrane lipids in patients with type 2 diabetes, Clin Chim Acta, Dec. 2001, 2 Pages, vol./Issue 314(1-2), Elsevier, U.S. Website: https://www.ncbi.nlm.nih.gov/pubmed/?term=Effect+of+mulberry+(Morus+indica+L.)+therapy+on+plasma+and+erythrocyte+membrane+lipids+in+patients+with+type+2+diabetes.
M.H.S. Jayawardena, et al., A double blind randomised placebo controlled cross over study of a herbal preparation containing Salacia reticulate in the treatment of type 2 diabetes, Journal of Ethnopharmacology, 2005, pp. 215-218, vol. 97, Elsevier Ireland Ltd., Ireland.
TA Clark, et al., Abstract: Effective control of glycemic status and toxicity in Zucker diabetic fatty rats with an orally administered vanadate compound, Can J Physiol Pharmacol, 2004, 2 Pages, vol./Issue 82(10), Canadian Journal of Physiology and Pharmacology, Canada. Website: https://www.ncbi.nlm.nih.gov/pubmed/?term=Effective+control+of+glycemic+status+and+toxicity+in+Zucker+diabetic+fatty+rats+with+an+orally+administered+vanadate+compound.
C. Shenoy, et al., Abstract: Hypoglycemic activity of bio-tea in mice, Indian J Exp Biol, Mar. 2000, 2 Pages, vol./Issue 38(3), Indian Journal of Experimental Biology, India. Website: https://www.ncbi.nlm.nih.gov/pubmed/?term=Hypoglycemic+activity+of+bio-tea+in+mice.+Indian+journal+of+experimental+biology+2000%2C.
JI Min Park, et al., Postprandial hypoglycemic effect of mulberry leaf in Goto-Kakizaki rats and counterpart control Wistar rats, Nutrition Research and Practice, 2009, pp. 272-278, vol./Issue 3(4), The Korean Nutrition Society and The Korean Society of Community Nutrition, Republic of Korea.
J. Naowaboot, et al., Abstract: Antihyperglycemic, antioxidant and antiglycation activities of mulberry leaf extract in streptozotocininduced chronic diabetic rats, Plant Foods Hum Nutr., Jun. 2009, 2 Pages, vol./Issue 64(2), Springer Nature Switzerland AG, Switzerland. Website: https://www.ncbi.nlm.nih.gov/pubmed/?term=Antihyperglycemic%2C+antioxidant+and+antiglycation+activities+of+mulberry+leaf+extract+in+streptozot%E2%80%A6.
Srikanta AH, et al., Abstract: The antioxidant effect of mulberry and jamun fruit wines by ameliorating oxidative stress in streptozotocin-induced diabetic Wistar rats, Food Funct., Oct. 12, 2016, 2 Pages, vol./Issue 7(10), Royal Society of Chemistry, U.K. Website: https://www.ncbi.nlm.nih.gov/pubmed/?term=The+antioxidant+effect+of+mulberry+and+jamun+fruit+wines+by+ameliorating+oxidative+stress+in+streptozotocin-induced+diabetic+Wistar+rats.
Attila Hunyadi, et al., Chlorogenic Acid and Rutin Play a Major Role in the In Vivo Anti-Diabetic Activity of Morus alba Leaf Extract on Type II Diabetic Rats, Nov. 2012, pp. 1-6, vol. 7, Issue 11, Plos One, U.S.
Tsuneyuki Oku, et al., Inhibitory effects of extractives from leaves of Morus alba on human and rat small intestinal disaccharidase activity, British Journal of Nutrition, 2006, pp. 933-938, vol. 95, Cambridge University Press, U.K.
C. Hansawasdi, et al., Abstract: Alpha-glucosidase inhibitory effect of mulberry (*Morus alba*) leaves on Caco-2, Fitoterapia., Dec. 2006, 2 Pages, vol./Issue 77(7-8), Elsevier, U.S. Website: https://www.ncbi.nlm.nih.gov/pubmed/?term=Alpha-glucosidase+inhibitory+effect+of+mulberry+(Morus+alba)+leaves+on+Caco-2.
B. Andallu, et al., Abstract: Antioxidant role of mulberry (*Morus indica* L. cv. *anantha*) leaves in streptozotocin-diabetic rats, Clin Chim Acta., Dec. 2003, 2 Pages, vol./Issue 338(1-2), Elsevier, U.S. Website: https://www.ncbi.nlm.nih.gov/pubmed/?term=Antioxidant+role+of+mulberry+(Morus+indica+L.+cv.+Anantha)+leaves+in+streptozotocin-diabetic+rats.
Yukihiro Kobayashi, et al., Ameliorative Effects of Mulberry (*Morus alba* L.) Leaves on Hyperlipidemia in Rats Fed a High-Fat Diet: Induction of Fatty Acid Oxidation, Inhibition of Lipogenesis, and Suppression of Oxidative Stress, Bioscience, Biotechnology, and Biochemistry, 2010, pp. 2385-2395, vol./Issue 74(12), Taylor & Francis Group, U.K.
Byambaa Enkhmaa, et al., Mulberry (*Morus alba* L.) leaves and their major flavonol quercetin 3-(6-malonylglucoside) attenuate atherosclerotic lesion development in LDL receptor-deficient mice, The Journal of Nutrition, 2005, pp. 729-734, vol./Issue 135(4), American Society for Nutritional Sciences, U.S.
Toshiyuki Kimura, et al., Food-Grade Mulberry Powder Enriched with 1-Deoxynojirimycin Suppresses the Elevation of Postprandial Blood Glucose in Humans, Journal of Agricultural and Food Chemistry, 2007, pp. 5869-5874, vol. 55, Issue 14, American Chemical Society, U.S.
Akira Asai, et al., Effect of mulberry leaf extract with enriched 1-deoxynojirimycin content on postprandial glycemic control in subjects with impaired glucose metabolism, Journal of Diabetes Investigation, Aug. 2011, pp. 318-323, vol. 2, Issue 4, Asian Association for the Study of Diabetes and Blackwell Publishing Asia Pty Ltd.
Litao Zhong, et al., An extract of black, green, and mulberry teas causes malabsorption of carbohydrate but not of triacylglycerol in healthy volunteers[1-3], The American Journal of Clinical Nutrition, 2006, pp. 551-555, vol. 84, American Society for Nutrition, U.S.
Slawomir Lewicki, et al., The role of Chromium III in the organism and its possible use in diabetes and obesity treatment, Review Article, 2014, pp. 331-335, vol. 21, Issue 2, Annals of Agricultural and Environmental Medicine, Poland.
William T. Cefalu, et al., Role of Chromium in Human Health and in Diabetes, Diabetes Care, Nov. 2004, pp. 2741-2751, vol. 27, Issue 11, The American Diabetes Association, U.S.
Joseph P. Fuhr Jr., et al., Abstract: Use of Chromium Picolinate and Biotin in the Management of Type 2 Diabetes: An Economic Analysis, Disease Management, Aug. 23, 2005, 2 Pages, vol. 8, Issue 4, Mary Ann Liebert, Inc., U.S.
N. Suksomboon, et al., Summary: Systematic review and meta-analysis of the efficacy and safety of chromium supplementation in diabetes, Journal of Clinical Pharmacy and Therapeutics, Mar. 17, 2014, 3 Pages, vol. 39, Issue 3, John Wiley & Sons, Inc. U.S.

(56) References Cited

OTHER PUBLICATIONS

Mohammad Abdollahi, et al., Effect of Chromium on Glucose and Lipid Profiles in Patients with Type 2 Diabetes; A Meta-analysis Review of Randomized Trials, J Pharm Pharmaceut Sci, Apr. 20, 2013, pp. 99-114, vol./Issue 16(1), Canadian Society for Pharmaceutical Sciences, Canada.

Yen-Lin Chen, et al., Abstract: The effect of chromium on inflammatory markers, 1st and 2nd phase insulin secretion in type 2 diabetes, European Journal of Nutrition, 2014, 2 Pages, vol./Issue 53(1), Springer Nature Switzerland AG, Switzerland. Website: https://www.ncbi.nlm.nih.gov/pubmed/?term=The+effect+of+chromium+on+inflammatory+markers%2C+1st+and+2nd+phase+insulin+secretion+in+type+2+diabetes.

S. Sharma, et al., Abstract: Beneficial effect of chromium supplementation on glucose, HbA1C and lipid variables in individuals with newly onset type-2 diabetes, J Trace Elem Med Biol., Jul. 2011, 2 Pages, vol./Issue 25(3), Elsevier, U.S. Website: https://www.ncbi.nlm.nih.gov/pubmed/?term=Beneficial+effect+of+chromium+supplementation+on+glucose%2C+HbA1C+and+lipid+variables+in+individuals+with+newly+onset+type-2+diabetes.

CC Lin, et al., Abstract: Chromium, zinc and magnesium status in type 1 diabetes, Curr Opin Clin Nutr Metab Care, Nov. 2015, 2 Pages, vol./Issue 18(6), U.S. National Library of Medicine National Institutes of Health, U.S. Website: https://www.ncbi.nlm.nih.gov/pubmed/?term=Chromium%2C+zinc+and+magnesium+status+in+type+1+diabetes.

H. Abunab, et al., Abstract: Effect of olive leaf extract on glucose levels in diabetes-induced rats: A systematic review and meta-analysis, J Diabetes, Dec. 26, 2016, 2 Pages, vol./Issue 9(10), Ruijin Hospital, Shanghai Jiaotong University School of Medicine and John Wiley & Sons Australia, Ltd., Australia. Website: https://www.ncbi.nlm.nih.gov/pubmed/?term=Effect+of+olive+leaf+extract+on+glucose+levels+in+diabetes-induced+rats%3A+A+systematic+review+a%E2%80%A6.

Julio Wainstein, et al., Abstract: Olive Leaf Extract as a Hypoglycemic Agent in Both Human Diabetic Subjects and in Rats, Journal of Medicinal Food, Jun. 26, 2012, 2 Pages, vol. 15, Issue 7, Mary Ann Liebert, Inc. U.S.

Martin De Bock, et al., Olive (*Olea europaea* L.) Leaf Polyphenols Improve Insulin Sensitivity in Middle-Aged Overweight Men: A Randomized, Placebo-Controlled, Crossover Trial, Mar. 13, 2013, pp. 1-8, vol. 8, Issue 3, Plos One, U.S.

AA Rashidi, et al., Abstract: Iranian medicinal plants for diabetes mellitus: a systematic review, May 1, 2013, 2 Pages, vol./Issue 16(9), Pakistan Journal of Biological Sciences, Pakistan. Website: https://www.ncbi.nlm.nih.gov/pubmed/24498803.

Hemant Poudyal, et al., Olive Leaf Extract Attenuates Cardiac, Hepatic, and Metabolic Changes in High Carbohydrate-, High Fat-Fed Rats[1-3], The Journal of Nutrition, Nutrition and Disease, Mar. 24, 2010, pp. 946-953, American Society for Nutrition, U.S.

R. Chebbi Mahjoub, et al., Chloroformic and Methanolic Extracts of *Olea europaea* L. Leaves Present Anti-Inflammatory and Analgesic Activities, International Scholarly Research Network, 2011, pp. 1-5, vol. 2011, ISRN Pharmacology, Tunisia.

P.M. Furneri, et al., Abstract: In vitro antimycoplasmal activity of oleuropein, Int J Antimicrob Agents, Oct. 2002, 1 Page, vol./Issue 20(4), Elsevier Science B.V. and International Society of Chemotherapy. Website: https://www.ncbi.nlm.nih.gov/pubmed/?term=In+vitro+antimycoplasmal+activity+of+oleuropein.

O.H. Lee, et al., Abstract: Antioxidant and antimicrobial activities of individual and combined phenolics in *Olea europaea* leaf extract, Bioresource Technology, May 2010, 2 Pages, vol./Issue 101(10), Elsevier Ltd., U.S. Website: https://www.ncbi.nlm.nih.gov/pubmed/?term=Antioxidant+and+antimicrobial+activities+of+individual+and+combined+phenolics+in+Olea+europaea+leaf+extract.

L. Wang, et al., Abstract: The anti-atherosclerotic effect of olive leaf extract is related to suppressed inflammatory response in rabbits with experimental atherosclerosis, European Journal of Nutrition, Aug. 2008, 2 Pages, vol./Issue 47(5), Springer Nature Switzerland AG, Switzerland. Website: https://www.ncbi.nlm.nih.gov/pubmed/?term=The+anti-atherosclerotic+effect+of+olive+leaf+extract+is+related+to+suppressed+inflammatory+response+in+rabbits+with+experimental+atherosclerosis.

Ahmet Cumaoğlu, et al., Effects of olive leaf polyphenols against $H_2O_2$ toxicity in insulin secreting β-cells, ACTA ABP Biochimica Polonica, 2011, pp. 45-50, vol. 58, Issue Jan. 2011, The Journal of the Polish Biochemical Society and of the Committee of Biochemistry and Biophysics Polish Academy of Sciences, Poland.

Y.N. Liu, et al., Abstract: Olive leaf extract suppresses messenger RNA expression of proinflammatory cytokines and enhances insulin receptor substrate 1 expression in the rats with streptozotocin and high-fat diet-induced diabetes, Nutrition Research, May 2014, 2 Pages, vol./Issue 34(5), Elsevier Inc., U.S. Website: https://www.ncbi.nlm.nih.gov/pubmed/?term=Olive+leaf+extract+suppresses+messenger+RNA+expression+of+proinflammatory+cytokines+and+enhances+insulin+receptor+substrate+1+expression+in+the+rats+with+streptozotocin+and+high-fat+diet-induced+diabetes.

A. Kaei Di, et al., Abstract: Olive (*Olea europaea* L.) leaf extract attenuates early diabetic neuropathic pain through prevention of high glucose-induced apoptosis: in vitro and in vivo studies, J Ethnopharmacol., Jun. 14, 2011, 2 Pages, vol./Issue 136(1), Elsevier Ireland Ltd., U.S. and Ireland. Website: https://www.ncbi.nlm.nih.gov/pubmed/?term=Olive+(Olea+europaea+L.)+leaf+extract+attenuates+early+diabetic+neuropathic+pain+through+prevention+of+high+glucose-induced+apoptosis%3A+in+vitro+and+in+vivo+studies.

Lawrence Leung, et al., Anti-diabetic and hypoglycaemic effects of *Momordica charantia* (bitter melon): a mini review, British Journal of Nutrition, 2009, pp. 1703-1708, vol. 102, Cambridge University Press, U.K.

I. Ahmed, et al., Abstract: Effects of *Momordica charantia* fruit juice on islet morphology in the pancreas of the streptozotocin-diabetic rat, Diabetes Research and Clinical Practice, Jun. 1998, 2 Pages, vol./Issue 40(3), Elsevier Inc., U.S. Website: https://www.ncbi.nlm.nih.gov/pubmed/?term=Effects+of+Momordica+charantia+fruit+juice+on+islet+morphology+in+the+pancreas+of+the+streptozotocindiabetic+rat.

P. Chaturvedi, et al., Abstract: Effect of Momordica charantia on lipid profile and oral glucose tolerance in diabetic rats, Phytotherapy Research, Nov. 2004, 2 Pages, vol./Issue 18(11), John Wiley & Sons, Inc., U.S. Website: https://www.ncbi.nlm.nih.gov/pubmed/15597317.

J. Welihinda, et al., Abstract: Effect of Momordica charantia on the glucose tolerance in maturity onset diabetes, Journal of Ethnopharmacology, Sep. 1986, 1 Page, vol./Issue 17(3), Elsevier, U.S. Website: https://www.ncbi.nlm.nih.gov/pubmed/3807390.

H.Y. Lo, et al., Abstract: Momordica charantia and its novel polypeptide regulate glucose homeostasis in mice via binding to insulin receptor, Journal of Agricultural and Food Chemistry, Mar. 13, 2013, 2 Pages, vol./Issue 61(10), American Chemical Society, U.S. Website: https://www.ncbi.nlm.nih.gov/pubmed/?term=Momordica+charantia+and+its+novel+polypeptide+regulate+glucose+homeostasis+in+mice+via+binding+to+insulin+receptor.

Ethan Basch, et al., Abstract: Bitter melon (*Momordica charantia*): A review of efficacy and safety, AJHP American Journal of Health-System Pharmacy, Feb. 15, 2003, pp. 1-6, vol. 60, Issue 4, Oxford University Press, U.K. Website: https://academic.oup.com/ajhp/article-abstract/60/4/356/5143141?redirectedFrom=fulltext.

Pratibha V. Nerurkar, et al., Momordica charantia (*bitter melon*) attenuates high-fat diet-associated oxidative stress and neuroinflammation, Journal of Neuroinflammation, 2011, pp. 1-19, vol./Issue 8:64, BioMed Central Ltd., U.S.

Pratibha V. Nerurkar, et al., *Momordica charantia* (bitter melon) reduces plasma apolipoprotein B-100 and increases hepatic insulin receptor substrate and phosphoinositide-3 kinase interactions, British Journal of Nutrition, 2008, pp. 751-759, vol. 100, Cambridge University Press, U.K.

M. G. Sridhar, et al., Bitter gourd (*Momordica charantia*) improves insulin sensitivity by increasing skeletal muscle insulin-stimulated IRS-1 tyrosine phosphorylation in high-fat-fed rats, British Journal of Nutrition, 2008, pp. 806-812, vol. 99, Cambridge University Press, U.K.

(56) References Cited

OTHER PUBLICATIONS

Z.Q. Wang, et al., Abstract: Bioactives from bitter melon enhance insulin signaling and modulate acyl carnitine content in skeletal muscle in high-fat diet-fed mice, The Journal of Nutritional Biochemistry, Nov. 2011, 2 Pages, vol./Issue 22(11), Elsevier Inc., U.S. Website: https://www.ncbi.nlm.nih.gov/pubmed/?term=Bioactives+from+bitter+melon+enhance+insulin+signaling+and+modulate+acyl+carnitine+content+in+skeletal+muscle+in+high-fat+diet-fed+mice.
Min-Jia Tan, et al., Antidiabetic Activities of Triterpenoids Isolated from Bitter Melon Associated with Activation of the AMPK Pathway, Chemistry & Biology, Mar. 2008, pp. 263-273, vol. 15, Elsevier Ltd.
Rachel H. H. Ching, et al., Supplementation of Bitter Melon to Rats Fed a High-Fructose Diet During Gestation and Lactation Ameliorates Fructose-Induced Dyslipidemia and Hepatic Oxidative Stress in Male Offspring[1-3], The Journal of Nutrition: Nutrient Physiology, Metabolism, and Nutrient-Nutrient Interactions, Aug. 3, 2011, pp. 1664-1672, American Society for Nutrition.
Padmaja Chaturvedi, et al., Momordica charantia Maintains Normal Glucose Levels and Lipid Profiles and Prevents Oxidative Stress in Diabetic Rats Subjected to Chronic Sucrose Load, Journal of Medicinal Food, Jun. 3, 2010, 2 Pages, vol. 13, No. 3, Mary Ann Liebert, Inc., USA.
D. Yadav, et al., Abstract: In vitro toxicity and antidiabetic activity of a newly developed polyherbal formulation (MAC-ST/001) in streptozotocin-induced diabetic Wistar rats, Protoplasma, Pubmed.gov, Sep. 28, 2012, 2 Pages, U.S. National Library of Medicine National Institutes of Health, U.S. Website: https://www.ncbi.nlm.nih.gov/pubmed/?term=In+vitro+toxicity+and+antidiabetic+activity+of+a+newly+developed+polyherbal+formulation+.
W. Nkambo, et al., In vivo hypoglycemic effect of methanolic fruit extract of *Momordica charantia* L, African Health Sciences, Dec. 2013, pp. 933-939, vol. 13, Issue 4, Department Of Pharmacy, School of Health Sciences, College of Health Sciences, Makerere University, Kampala Uganda.
Razif Abas, et al., Protective Effect of *Momordica charantia* Fruit Extract on Hyperglycaemia-Induced Cardiac Fibrosis, Oxidative Medicine and Cellular Longevity, Oct. 13, 2014, pp. 1-8, vol. 2014, Hindawi Publishing Corporation.
Divya Khaitan, et al., Differential mechanisms of radiosensitization by 2-deoxy-D-glucose in the monolayers and multicellular spheroids of a human glioma cell line, Cancer Biology & Therapy, 2006, pp. 1142-1151, vol. 5, Issue 9, Landes Bioscience.
Neelam K. Venkataramanaa et al., Protective effect on normal brain tissue during a combinational therapy of 2-deoxy-d-glucose and hypofractionated irradiation in malignant gliomas, Jan.-Mar. 2013, pp. 9-14, vol. 8, Issue 1, Asian Journal of Neurosurgery.
Y. Wu, et al., Abstract: Combined inhibition of glycolysis and AMPK induces synergistic breast cancer cell killing, Breast Cancer Res Treat, Pubmed.gov, May 15, 2015, 2 Pages, U.S. National Library of Medicine National Institutes of Health, U.S. Website: https://www.ncbi.nlm.nih.gov/pubmed/?term=Combined+inhibition+of+glycolysis+and+AMPK+induces+synergistic+breast+cancer+cell+killing.
Yong Wu, et al., High glucose-induced p53 phosphorylation contributes to impairment of endothelial antioxidant system, BBA—Molecular Basis of Disease, Jun. 30, 2017, pp. 2355-2362, vol./Issue 1863, Elsevier B.V.
Yong Wu, et al., Phosphorylation of p53 by TAF1 Inactivates p53-Dependent Transcription in the DNA Damage Response, Molecular Cell Article, Jan. 9, 2014, pp. 63-74, vol. 53, Elsevier Inc.
Saurabh Singh, et al., Chronic Dietary Administration of the Glycolytic Inhibitor 2-Deoxy-D-Glucose (2-DG) Inhibits the Growth of Implanted Ehrlich's Ascites Tumor in Mice, Plos One, Jul. 2, 2015, pp. 1-19, Singh et al., India.
Ruiqian Wan, et al., Intermittent fasting and dietary supplementation with 2-deoxy-D-glucose improve functional and metabolic cardiovascular risk factors in rats, The FASEB Journal Express Article, Apr. 22, 2003, 19 Pages, The FASEB Journal, U.S.

Raez Le, et al., Abstract: A phase I dose-escalation trial of 2-deoxy-D-glucose alone or combined with docetaxel in patients with advanced solid tumors, Cancer Chemother Pharmacol, Pubmed.gov, Dec. 11, 2012, 2 Pages, U.S. National Library of Medicine National Institutes of Health, U.S. Website: https://www.ncbi.nlm.nih.gov/pubmed/23228990.
Verhave G. Siegert CE, Abstract: Role of vitamin D in cardiovascular disease, The Netherlands Journal of Medicine, Feb. 28, 2010, 2 Pages, vol. 68, Issue 3, PMC International archive, Netherlands. Website: https://europepmc.org/article/med/20308705.
M. Hewison, Abstract: Vitamin D and the immune system: new perspectives on an old theme, Endocrinol Metab Clin North Am, Pubmed.gov, 2010, 2 Pages, U.S. National Library of Medicine National Institutes of Health, U.S., Elsevier Inc., U.S. Website: https://www.ncbi.nlm.nih.gov/pubmed/20511058.
Christian Herr, et al., The role of vitamin D in pulmonary disease: COPD, asthma, infection, and cancer, Respiratory Research, 2011, pp. 1-9, vol./Issue 12:31, BioMed Central Ltd., Germany.
Armin Zittermann, et al., Nonclassical Vitamin D Actions, Nutrients, Mar. 25, 2010, pp. 408-425, vol. 2, Molecular Diversity Preservation International, Basel, Switzerland.
Surya Prakash Bhatt, et al., Lower vitamin D levels are associated with higher blood glucose levels in Asian Indian women with pre-diabetes: a population-based cross-sectional study in North India, Jun. 15, 2018, pp. 1-9, BMJ Open Diabetes Research Care, India.
Mattia Bellan, et al., Altered glucose metabolism rather than naive type 2 diabetes mellitus (T2DM) is related to vitamin D status in severe obesity, Cardiovascular Diabetology, 2014, pp. 1-10, vol./Issue 13:57, BioMed Central Ltd., Italy.
Mohamad Mi, et al., Abstract: The Effect of Vitamin D Supplementation on Glycemic Control and Lipid Profile in Patients with Type 2 Diabetes Mellitus, J Am Coll Nutr, Pubmed.gov, Sep. 21, 2015, 2 Pages, U.S. National Library of Medicine National Institutes of Health, U.S. Website: https://www.ncbi.nlm.nih.gov/pubmed/?term=The+Effect+of+Vitamin+D+Supplementation+on+Glycemic+Control+and+Lipid+Profile+in+Patients+with%E2%80%A6.
Yvonne H M Krul-Poel, et al., The effect of vitamin D supplementation on glycaemic control in patients with type 2 diabetes mellitus: a systematic review and meta-analysis, European Journal of Endocrinology, 2017, pp. R1-R14, vol./Issue 176:1, Bioscientifica Ltd., Great Britain.
CJ Lee, et al., Abstract: The effect of vitamin D supplementation on glucose metabolism in type 2 diabetes mellitus: A systematic review and meta-analysis of intervention studies, J Diabetes Complications, Pubmed.gov, Apr. 21, 2017, 2 Pages, U.S. National Library of Medicine National Institutes of Health, U.S. Website: https://www.ncbi.nlm.nih.gov/pubmed/28483335.
M. Grammatiki, et al., Abstract: Vitamin D and diabetes mellitus: Causal or casual association?, Rev Endocr Metab Disord, Pubmed.gov, 2017, 2 Pages, U.S. National Library of Medicine National Institutes of Health, U.S. Website: https://www.ncbi.nlm.nih.gov/pubmed/28062940.
Gregory M. Singer, et al., Abstract: The Effect of Chromium Picolinate and Biotin Supplementation on Glycemic Control in Poorly Controlled Patients with Type 2 Diabetes Mellitus: A Placebo-Controlled, Double-Blinded, Randomized Trial, Diabetes Technology & Therapeutics, Nov. 16, 2006, 2 Pages, vol. 8, No. 6, Mary Ann Liebert, Inc., U.S. Website: https://www.liebertpub.eom/doi/abs/10.1089/dia.2006.8.636.
CA Albarracin, et al., Abstract: Chromium picolinate and biotin combination improves glucose metabolism in treated, uncontrolled overweight to obese patients with type 2 diabetes, Diabetes Metab Res Rev, Pubmed.gov, Jan.-Feb. 2008, 2 Pages, U.S. National Library of Medicine National Institutes of Health, U.S. Website: https://www.ncbi.nlm.nih.gov/pubmed/?term=Chromium+picolinate+and+biotin+combination+improves+glucose+metabolism+in+treated%2C+uncontr%E2%80%A6.
CA Albarracin, et al., Abstract: Combination of chromium and biotin improves coronary risk factors in hypercholesterolemic type 2 diabetes mellitus: a placebo-controlled, double-blind randomized clinical trial, J Cardiometab Syndr, Pubmed.gov, Spring 2007, 2 Pages, U.S. National Library of Medicine National Institutes of

(56) References Cited

OTHER PUBLICATIONS

Health, U.S. Website: https://www.ncbi.nlm.nih.gov/pubmed/?term=Combination+of+chromium+and+biotin+improves+coronary+risk+factors+in+hypercholesterolemic+type+%E2%80%A6.

G. Paolisso, et al., Abstract: Plasma vitamin C affects glucose homeostasis in healthy subjects and in non-insulin-dependent diabetics, Am J Physiol, Pubmed.gov, Feb. 1994, 2 Pages, U.S. National Library of Medicine National Institutes of Health, U.S. Website: https://www.ncbi.nlm.nih.gov/pubmed/?term=Plasma+vitamin+C+affects+glucose+homeostasis+in+healthy+subjects+and+in+non-insulin-dependent+%E2%80%A6.

J. Kositsawat, et al., Abstract: Vitamin C and A1c relationship in the National Health and Nutrition Examination Survey (NHANES) 2003-2006, J Am Coll Nutr, Pubmed.gov, Dec. 2011, 2 Pages, U.S. National Library of Medicine National Institutes of Health, U.S. Website: https://www.ncbi.nlm.nih.gov/pubmed/?term=Vitamin+C+and+A1c+relationship+in+the+National+Health+and+Nutrition+Examination+Survey+.

Ganesh N. Dakhale, et al., Supplementation of Vitamin C Reduces Blood Glucose and Improves Glycosylated Hemoglobin in Type 2 DiabetesMellitus: A Randomized, Double-Blind Study, Advances in Pharmacological Sciences, 2011, 5 Pages, vol. 2011, Hindawi Publishing Corporation, India.

Jonas Cederberg, et al., Combined Treatment with Vitamin E and Vitamin C Decreases Oxidative Stress and Improves Fetal Outcome in Experimental Diabetic Pregnancy, 2001, pp. 755-762, vol. 49, No. 6, International Pediatric Research Foundation, Inc., U.S.

M. Kutlu, et al., Abstract: Moderate exercise combined with dietary vitamins C and E counteracts oxidative stress in the kidney and lens of streptozotocin-induced diabetic-rat, Int J Vitam Nutr Res, Pubmed.gov, Jan. 2005, 2 Pages, U.S. National Library of Medicine National Institutes of Health, U.S. Website: https://www.ncbi.nlm.nih.gov/pubmed/?term=Moderate+exercise+combined+with+dietary+vitamins+C+and+E+counteracts+oxidative+stress+in+the+k%E2%80%A6.

YH Abdel-Wahab, et al., Abstract: Vitamin C supplementation decreases insulin glycation and improves glucose homeostasis in obese hyperglycemic (ob/ob) mice, Metabolism, Pubmed.gov, Apr. 2002, 2 Pages, U.S. National Library of Medicine National Institutes of Health, U.S. Website: https://www.ncbi.nlm.nih.gov/pubmed/?term=Vitamin+C+supplementation+decreases+insulin+glycation+and+improves+glucose+homeostasis+in+obe%E2%80%A6.

M. Khodaeian, et al., Abstract: Effect of vitamins C and E on insulin resistance in diabetes: a meta-analysis study, Eur J Clin Invest, Pubmed.gov, Sep. 21, 2015, 2 Pages, U.S. National Library of Medicine National Institutes of Health, Stichting European Society for Clinical Investigation Journal Foundation, U.S. Website: https://www.ncbi.nlm.nih.gov/pubmed/?term=Effect+of+vitamins+C+and+E+on+insulin+resistance+in+diabetes%3A+a+meta-analysis+study.

Ozra Tabatabaei-Malazy, et al., Influence of Ascorbic Acid Supplementation on Type 2 Diabetes Mellitus in Observational and Randomized Controlled Trials; A Systematic Review with Meta-Analysis, 2014, pp. 554-582, vol./Issue 17(4), J Pharm Pharm Sci, Canada.

Julie C. Will, et al., Does Diabetes Mellitus Increase the Requirement for Vitamin C?, Lead Review Article, Jul. 1, 1996, pp. 193-202, vol. 54, No. 7, Nutrition Reviews, U.S. Website: https://academic.oup.eom/nutritionreviews/article/54/7/193/1821533.

* cited by examiner

DIETARY SUPPLEMENT FOR GLYCEMIA CONTROL AND DIABETES PREVENTION

CROSS-REFERENCE TO RELATED APPLICATION(S)

This application is a continuation-in-part application of U.S. patent application Ser. No. 16/231,200, filed on Dec. 21, 2018, which claims priority to and the benefit of U.S. Provisional Patent Application No. 62/767,471, filed on Nov. 14, 2018, the entire contents of which are incorporated herein by reference.

BACKGROUND

Field

The present disclosure relates to a dietary supplement for controlling postprandial blood glucose, increasing insulin sensitivity and/or assisting in the glucose metabolism for individuals with impaired glucose tolerance (IGT), pre-diabetes and metabolic syndrome.

Description of the Related Art

With the rapid development of social economy and the aging of population, people's diet, nutrition and lifestyle have also undergone substantial changes. High-calorie, high-fat, high-sugar, high-salt diets and consumption of sweetened beverages, including diet soda, have significantly increased. On the other hand, physical activity levels have significantly decreased and sedentary lifestyle is very common. All these have contributed to the prevalence of chronic non-communicable diseases, such as overweight, obesity, pre-diabetes, diabetes and so on all over the world. The incidence of diabetes has increased significantly, becoming the third serious chronic disease after cancer and cardiovascular diseases.

Although Acarbose, Metformin and 1-deoxynojirimycin have good clinical efficacy as hypoglycemic agents, their high cost and some serious side effects limit their clinical application. Thus, there is an urgent need for natural, botanical strategies to prevent the development of diabetes. Plants have always been a useful source of medicine, and many of the existing drugs are directly or indirectly derived from plants. It is of great significance to study the hypoglycemic effect of plants originally utilized in traditional medicine.

The above information disclosed in this Background section is only for enhancement of understanding of the background of the invention, and therefore it may contain information that does not form the prior art that is already known to a person of ordinary skill in the art.

SUMMARY

An aspect of embodiments of the present invention is directed toward a dietary supplement that inhibits glucose absorption, controls postprandial blood glucose, increases insulin sensitivity and/or enhances glucose metabolism for patients with metabolic syndrome.

Metabolic syndrome is a series of metabolic abnormalities, including abdominal obesity, insulin resistance, atherosclerotic dyslipidemia, increased blood pressure, and inflammation, which are related to type 2 diabetes, cardiovascular disease and/or increased mortality. The prevalence of these clustering abnormalities has been progressively growing over the past 20 years, and now it is estimated that more than a third of American adults, especially older adults, are affected.

An aspect of embodiments of the present invention is directed toward a dietary supplement containing various herbal extracts, vitamins, 2-deoxy-D-glucose and trace element as a nutritional strategy for the prevention and treatment of insulin resistance and type 2 diabetes mellitus (T2DM).

Another aspect of embodiments of the present invention is directed toward a method of preventing and treating insulin resistance and T2DM utilizing a botanical formula.

According to some embodiments of the present disclosure, a formulation for a dietary supplement includes standardized extracts of *astragalus* root, phlorizin, root bark of white mulberry, olive leaf, and bitter melon.

The standardized extracts of *astragalus* root, phlorizin, root bark of white mulberry, olive leaf, and bitter melon may be included at a ratio of 1:1.8:3.2:1.6:1.2.

The formulation may further include chromium, 2-deoxy-D-glucose, biotin, vitamin D and vitamin C.

The formulation may include 8% of standardized extract of *astragalus* root, 14.4% of phlorizin, 25.6% of standardized extract of root bark of white mulberry, 12.8% of standardized extract of olive leaf, 9.6% of standardized extract of bitter melon, 25.6% of 2-deoxy-D-glucose, 0.1% of biotin, 3.8% of vitamin C, and trace amount of chromium picolinate and vitamin D, based on a total weight of the formulation.

The dietary supplement may be for oral consumption. The dietary supplement may be a tablet, a soft or hard capsule, liquid, or a suspension According to some embodiments of the present disclosure, a method of controlling postprandial blood glucose includes administering a formulation for a dietary supplement to a patient, the formulation containing standardized extracts of *astragalus* root, phlorizin, root bark of white mulberry, olive leaf, and bitter melon.

The standardized extracts of *astragalus* root, phlorizin, root bark of white mulberry, olive leaf, and bitter melon may be included at a ratio of 1:1.8:3.2:1.6:1.2.

The formulation may further include chromium, 2-deoxy-D-glucose, biotin, vitamin D and vitamin C.

The formulation may include 8% of standardized extract of *astragalus* root, 14.4% of phlorizin, 25.6% of standardized extract of root bark of white mulberry, 12.8% of standardized extract of olive leaf, 9.6% of standardized extract of bitter melon, 25.6% of 2-deoxy-D-glucose, 0.1% of biotin, and 3.8% of vitamin C based on a total weight of the formulation.

The administering may be through oral consumption.

The administering may be repeated twice per day before meals, and a total weight of the formulation is about 780 mg.

The patient may have one or more of obesity, impaired glucose tolerance, pre-diabetes and diabetes.

According to some embodiments of the present disclosure, a formulation for a dietary supplement includes standardized extracts of *astragalus* root, phlorizin, root bark of white mulberry, olive leaf, bitter melon, and 2-deoxy-D-glucose.

The standardized extracts of *astragalus* root, phlorizin, root bark of white mulberry, olive leaf, and bitter melon may be included at a ratio of 1:1.8:3.2:1.6:1.2.

The formulation may further include biotin and vitamin C.

The formulation may include 8% of standardized extract of *astragalus* root, 14.4% of phlorizin, 25.6% of standardized extract of root bark of white mulberry, 12.8% of standardized extract of olive leaf, 9.6% of standardized extract of bitter melon, 25.6% of 2-deoxy-D-glucose, 0.1% of biotin, and 3.8% of vitamin C.

The dietary supplement may be for oral consumption. The dietary supplement may be a tablet, a soft or hard capsule, liquid, or a suspension.

According to some embodiments of the present disclosure, alpha-lipoic acid is utilized in place of (i.e., to replace) 2-deoxy-D-glucose in the formulation for a dietary supplement at the same amount as the 2-deoxy-D-glucose.

According to some embodiments of the present disclosure, a method of controlling postprandial blood glucose includes administering to a patient the formulation for the dietary supplement according to some embodiments of the present disclosure.

BRIEF DESCRIPTION OF THE DRAWINGS

The accompanying drawings, together with the specification, illustrates example embodiments of the present invention, and, together with the description, serves to explain the principles of the present invention.

DETAILED DESCRIPTION

Figure 1:
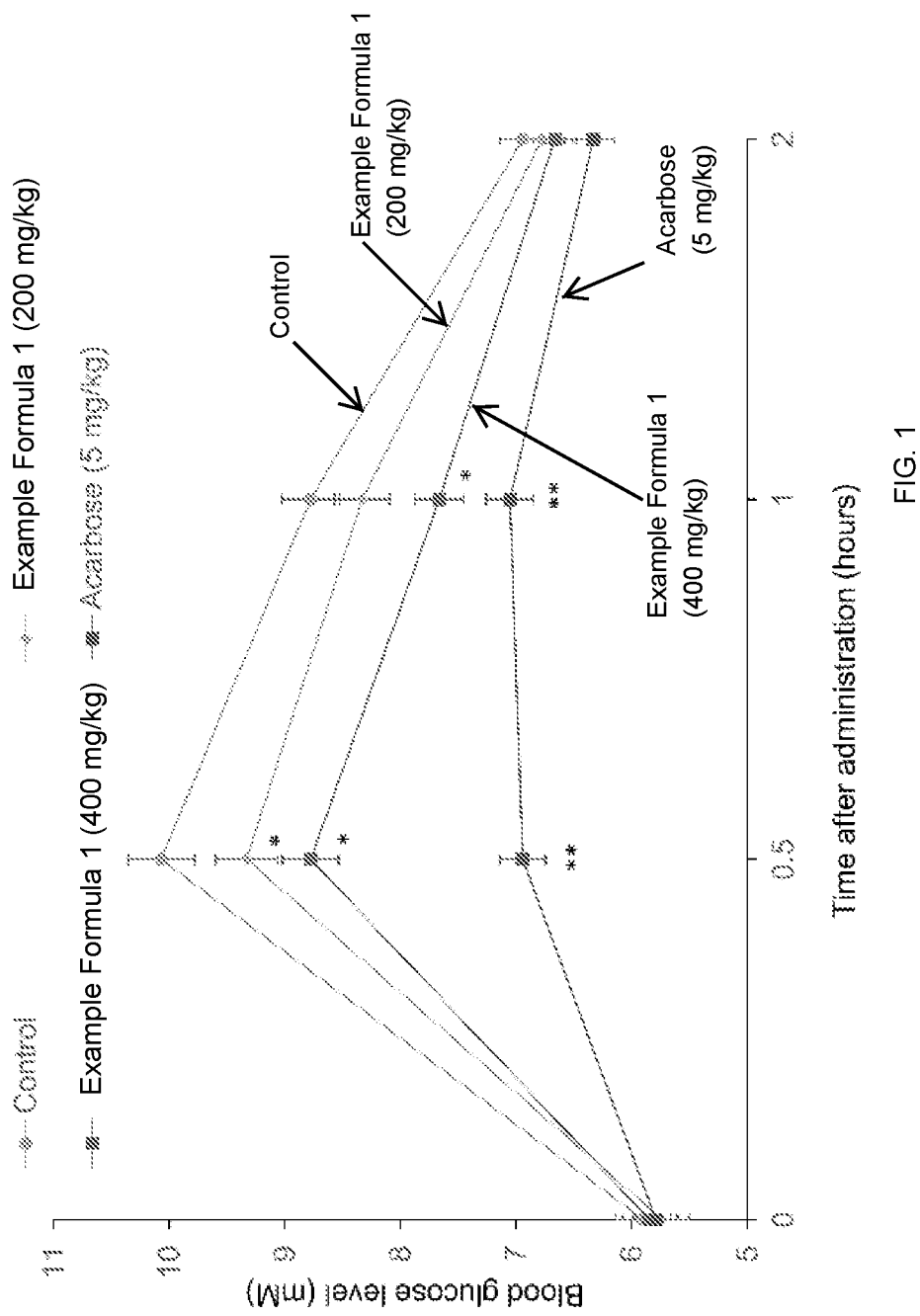
FIG. 1 shows the effect of different dosage of Example Formula 1 on sucrose loading test.

In the following detailed description, only certain exemplary embodiments of the present invention are shown and described, by way of illustration. As those skilled in the art would recognize, the invention may be embodied in many different forms and should not be construed as being limited to the embodiments set forth herein. Descriptions of features or aspects within each exemplary embodiment should typically be considered as applicable to other similar features or aspects in other exemplary embodiments. Like reference numerals designate like elements throughout the specification.

According to some embodiments of the present disclosure, a botanical formula includes standardized extracts of *astragalus* root, phlorizin, root bark of white mulberry, olive leaf, and bitter melon.

The standardized extracts of *astragalus* root, phlorizin, root bark of white mulberry, olive leaf, and bitter melon may be included at a ratio (a weight ratio) of 1:1.8:3.2:1.6:1.2.

According to some embodiments of the present disclosure, a formulation for a dietary supplement includes standardized extracts of *astragalus* root, phlorizin, root bark of white mulberry, olive leaf, and bitter melon.

The standardized extracts of *astragalus* root, phlorizin, root bark of white mulberry, olive leaf, and bitter melon may be included at a ratio of 1:1.8:3.2:1.6:1.2.

The formulation for the dietary supplement may further include chromium, 2-deoxy-D-glucose, biotin, vitamin D and vitamin C.

According to some embodiments of the present disclosure, a formulation for a dietary supplement includes 7.21 to 8.81 wt % of standardized extract of *astragalus* root, 12.96 to 15.84 wt % of phlorizin, 23.04 to 28.16 wt % of standardized extract of root bark of white mulberry, 11.52 to 14.08 wt % of standardized extract of olive leaf, 8.64 to 10.56 wt % of standardized extract of bitter melon, 23.04 to 28.16 wt % of at least one selected from 2-Deoxy-D-glucose and alpha-lipoic acid, 0.09 to 0.11 wt % of biotin, 3.42 to 4.18 wt % of vitamin C, and trace amount of chromium and vitamin D, each based on a total weight of the formulation.

The formulation for the dietary supplement may include 8.01% of standardized extract of *astragalus* root, 14.41% of phlorizin, 25.62% of standardized extract of root bark of white mulberry, 12.81% of standardized extract of olive leaf, 9.61% of standardized extract of bitter melon, 25.62% of 2-deoxy-D-glucose and/or alpha-lipoic acid, 0.06% of biotin, 3.84% of vitamin C, and trace amount (i.e., less than 0.1%) of chromium picolinate and vitamin D, based on a total weight of the formulation.

According to some embodiments of the present disclosure, the formulation for the dietary supplement may further include alpha-lipoic acid. In one or more embodiments, alpha-lipoic acid may be utilized in place of 2-deoxy-D-glucose.

The formulation for the dietary supplement may include 8.01% of standardized extract of *astragalus* root, 14.41% of phlorizin, 25.62% of standardized extract of root bark of white mulberry, 12.81% of standardized extract of olive leaf, 9.61% of standardized extract of bitter melon, 25.62% of alpha-lipoic acid, 0.06% of biotin, 3.84% of vitamin C, and trace amount (i.e., less than 0.1%) of chromium picolinate and vitamin D, based on a total weight of the formulation.

According to some embodiments of the present disclosure, a formulation for a dietary supplement includes standardized extracts of *astragalus* root, phlorizin, root bark of white mulberry, olive leaf, bitter melon, and 2-deoxy-D-glucose.

The standardized extracts of *astragalus* root, phlorizin, root bark of white mulberry, olive leaf, and bitter melon may be included at a ratio of 1:1.8:3.2:1.6:1.2.

The formulation may further include biotin and vitamin C.

The formulation may include 8.01% of standardized extract of *astragalus* root, 14.41% of phlorizin, 25.62% of standardized extract of root bark of white mulberry, 12.81% of standardized extract of olive leaf, 9.61% of standardized extract of bitter melon, 25.62% of 2-deoxy-D-glucose, 0.06% of biotin, and 3.84% of vitamin C.

According to some embodiments of the present disclosure, a method of controlling postprandial blood glucose includes administering a formulation for a dietary supplement, the formulation for the dietary supplement containing standardized extracts of *astragalus* root, phlorizin, root bark of white mulberry, olive leaf, and bitter melon.

The standardized extracts of *astragalus* root, phlorizin, root bark of white mulberry, olive leaf, and bitter melon may be included at a ratio of 1:1.8:3.2:1.6:1.2.

The formulation for the dietary supplement may further include chromium, 2-deoxy-D-glucose, biotin, vitamin D and vitamin C.

The formulation for the dietary supplement may include about 8% of standardized extract of *astragalus* root, 14.4% of phlorizin, 25.6% of standardized extract of root bark of white mulberry, 12.8% of standardized extract of olive leaf, 9.6% of standardized extract of bitter melon, 25.6% of 2-deoxy-D-glucose, 0.1% of biotin, 3.8% of vitamin C, and trace amount (i.e., less than 0.1%) of chromium picolinate and vitamin D, based on a total weight of the formulation for the dietary supplement.

According to some embodiments of the present disclosure, the formulation for the dietary supplement may further include alpha-lipoic acid. In one or more embodiments, alpha-lipoic acid may be utilized in place of 2-deoxy-D-glucose.

The formulation for the dietary supplement may include about 8% of standardized extract of *astragalus* root, 14.4% of phlorizin, 25.6% of standardized extract of root bark of white mulberry, 12.8% of standardized extract of olive leaf, 9.6% of standardized extract of bitter melon, 25.6% of alpha-lipoic acid, 0.1% of biotin, 3.8% of vitamin C, and trace amount (i.e., less than 0.1%) of chromium picolinate and vitamin D, based on a total weight of the formulation.

Without being bond by any particular theory, the function of each component in the dietary supplement is described as following.

*Astragalus*

It is believed that *astragalus*, also known as huang qi or milk vetch, has a function of enhancing the body's immune system. It has also been utilized to treat other diseases, such as heart disease. While there are several species of *astragalus*, most *astragalus* supplements contain *Astragalus membranaceus*. The plant *A membranaceus* has been traditionally utilized as an infusion of (mainly) roots by the Chinese population to treat type II diabetes. Furthermore, *A membranaceus* is an important component of the majority of traditional herbal blend prescriptions utilized to cure type II diabetes in traditional Chinese medicine.

Subjected to sequential extraction, it was discovered that the maximum activity of *A membranaceus* lies in *astragalus* polysaccharides (APS). For example, APS has been found to enable insulin-sensitizing and hypoglycemic activity by decreasing the elevated expression and activity of protein tyrosine phosphatase 1B (PTP1B), a negative regulator of insulin-receptor (IR) signal transduction, in the skeletal muscles of type 2 diabetic rats. In addition, APS can significantly inhibit the α-glucosidase activity, reducing the conversion of disaccharide, polysaccharide and other substances in food into absorbable monosaccharide, which ultimately inhibits the rise of blood glucose after meals. Further studies indicated that astragaloside, another bioactive component of *astragalus*, improved TNFα-induced insulin resistance in 3T3-L1 adipocytes and increases insulin sensitivity. Therefore, standardized extract of *astragalus* is utilized in the dietary supplement for prevention and treatment for diabetes, according to embodiments of the present disclosure.

Phlorizin

Phlorizin, a molecule found in the root bark, leaves, shoots and fruit of the apple tree, has been found to inhibit glucose absorption in small intestine and promote urinary glucose excretion in healthy humans. Sodium-glucose co-transporters SGLT1 and SGLT2 are imperative mediators of epithelial glucose transport. SGLT1 accounts for most of the dietary glucose uptake in the intestine. SGLT2 is responsible for the majority of glucose re-absorption in renal tubular system, with SGLT1 reabsorbing the remainder of the filtered glucose. Rodent studies have demonstrated that diabetes increases intestinal SGLT1 expression and glucose absorption, thus leading to postprandial hyperglycemia. Consistent with this, pre-meal instead of post-meal, oral administration of the selective SGLT1 inhibitor GSK-1614235 can delay intestinal glucose absorption in healthy volunteers.

Inhibition of intestinal SGLT1 has dual effects on glucose homeostasis: (1) by suppressing glucose uptake directly, and (2) by stimulating the continuous release of hypoglycemic hormones indirectly. The renal proximal tubule re-uptakes all the filtered glucose in healthy adults (about 180 g/day). SGLT2 is expressed in the early proximal tubules, accounting for the whole glucose re-absorption in this section and for about 97% of the total renal fractional glucose reabsorption (FGR). In contrast, SGLT1 is expressed in the latter half of the proximal tubule, accounting for about 3% of FGR. Therefore, under normal physiological conditions, SGLT2 and SGLT1 are responsible for all glucose reabsorption in kidney.

Diabetes may moderately enhance the maximum renal reabsorption of glucose due to elevated expression of SGLT2 or SGLT1. Thus, SGLT2 inhibition can help maintain glucose homeostasis in the normoglycemic and moderately hyperglycemic range. Therefore, targeting hyperglycemia through suppressing intestinal or kidney glucose re-absorption is a desirable therapeutic strategy.

Phlorizin is a natural competitive inhibitor of SGLT1 and SGLT2. It has been found that subcutaneous administration of phlorizin normalizes blood glucose levels and insulin sensitivity in diabetic rats with insulin resistance.

White Mulberry

For centuries, white mulberry (*Morus alba*) has been utilized in traditional Chinese medicine to treat diabetes, atherosclerosis, cancer and to enhance the immune system due to its effective antioxidant activity. Different parts of mulberry trees (e.g., fruits, bark, leaves and roots) have attracted interest in their treatment of diabetes because the roots and bark are often utilized to decrease hyperglycemia. Mulberry extract can decrease blood glucose in type 2 diabetic patients and in diabetic animal models. This hypoglycemic effect is usually attributed to changes in the intermediary metabolism of glucose. For example, various alkaloids, flavonoids and phytochemicals in mulberry leaves have been found to have anti-diabetic effects. These effects are associated with repression of alpha-glucosidase, sucrase and maltase activities, reduction of carbohydrate metabolism and consequently depressing of blood glucose levels, hindrance of lipid peroxidation, improvement of dyslipidemia, particularly hypercholesterolemia, and inhibition of LDL cholesterol oxidation. 1-deoxynojirimycin (DNJ), an alkaloid in white mulberry leaves, has been reported to have an activity of lowering non-fasting blood glucose (NFBG) in humans. Moreover, DNJ is also a glucose analogue and a promising alpha-glucosidase inhibitor. A human study demonstrated that long-term intake of mulberry leaf extract containing DNJ can improve postprandial glycemic control in individuals with impaired glucose metabolism.

Chromium

Chromium (Cr) is a ubiquitous metal existing in water, soil and biological systems. The three most stable forms of Cr in the environment are metal and alloys, trivalent Cr (Cr III), and hexavalent Cr (Cr VI). This trace element participates in the metabolism of carbohydrates, lipids and proteins primarily through augmenting the efficacy of insulin. Cr deficiency disturbs normal glucose tolerance and healthy blood lipid levels. Trivalent Cr is considered an indispensable element in animal feeding and human nutrition. It has been shown that Cr can stimulate insulin receptors, activate hepatic enzyme glucokinase, and enhance islet B cells.

Positive effects of Cr on human or animals have been reported. It has been showed that Cr III, as an active component of glucose tolerance factor (GTF), could control impaired glucose tolerance in rats. Further, the use of Cr III in parenteral nutrition was shown to relieve severe diabetic symptoms in women. A meta-analysis study aiming to illuminate the effect of Cr on the glucose and lipid profiles among type 2 diabetes mellitus (T2DM) patients demonstrates that Cr supplementation strikingly decreases fasting blood sugar (FBS). This may be explained by the fact that chromium can control hyperglycemia in T2DM because of increased insulin action. Compromised insulin sensitivity (SI) and β-cell function are the two crucial causes of T2DM. Trivalent Cr has shown to increase SI and chromium chloride (CrCl) could also promote the second phase of insulin responsivity in T2DM. In addition, Cr affects glucose metabolism through enhancing the action of insulin signaling amplification mechanism. A placebo-controlled single blind, prospective study carrying out to explore the effect of Cr supplementation on blood glucose, HbA(1)C and lipid profile in newly onset patients with T2DM further substantiates the beneficial effect of Cr supplementation on glycemic control and lipid variables. Of note, more recently, a systematic review and meta-analysis aiming to evaluate the effects on metabolic profiles and safety of Cr supplementation in diabetes also suggest favorable effects of Cr supplementation on glycemic control in diabetic patients. Cr mono-supplement can also improve triglycerides and HDL-C levels. Compared with placebo, regular doses of Cr supplementation do not elevate the risk of adverse events. Lastly, more and more studies have shown that the decrease in serum Cr levels is positively correlated with impaired glycemic control.

Olive Leaf Extract

Many people in the Middle East North Africa (MENA) countries utilize traditional alternatives, such as herbs and leaves, to treat various diseases. Olive tree is one of the many native plants that are abundant in MENA countries. It is not only utilized for food, but also extensively utilized in different ways to treat a variety of diseases, including diabetes. People tend to utilize these alternatives to control different types of diseases because they are reported to have anti-oxidant and anti-inflammatory properties, as well as specific insulin sensitization effects.

The usage of olive leaf extract (OLE) to manage diabetes is an alternative diabetes treatment method. The leaves of *Olea europaea* L. contain a large number of bioactive compounds. Among them, phenolic compounds, such as oleuropein and hydroxytyrosol, can promote insulin secretion, beta cell viability, and have hypoglycemic, anti-oxidant and anti-inflammatory effects. In addition, olive leaves have anti-nociceptive activity and are utilized as antibiotics for bacteria, molds and *mycoplasma* infections. Active ingredients of olive leaf, for example, tocopherol, oleuropein, caffeic acid, and luteolin, have been studied as potential diabetes-preventive components for lowering blood sugar levels, restoring hyperglycemic symptoms and enhancing antioxidant activity. It has been found that OLE can effectively restore atherosclerosis through inhibiting the expression of TNF-alpha in rabbits with experimental atherosclerosis. In vitro studies utilizing INS-1 cells reveal that OLE and olivopicrin enhance the number of living cells and the levels of anti-oxidant enzymes. Further, OLE can reduce insulin resistance via inhibiting the expression of pro-inflammatory cytokine mRNA and increasing the expression of insulin receptor substrate 1. Furthermore, OLE can hinder high glucose-triggered neural damage and diabetes-induced hyperalgesia. Without being bond by any particular theory, the mechanisms may be at least partly due to the reduction of neuronal apoptosis, implying the therapeutic potential of OLE in reducing diabetic neuropathic pain. Supplementation with OLE has shown to strikingly improve insulin sensitivity and pancreatic beta-cell secretory ability in overweight middle-aged men, who are at risk of developing metabolic syndrome. Results also show that taking OLE (e.g., 500 mg OLE tablet once a day for 14 weeks) is related to improving glucose homeostasis in humans with T2DM.

Animal studies suggest that this effect may be facilitated via the inhibition of starch digestion and absorption. More recently, a systematic review and meta-analysis of randomized control trials aiming to evaluate the effects of OLE on the glucose and insulin levels demonstrate that it is favorable for both the lipid profile and blood glucose control in diabetic rats and also may be equally effective in humans. Therefore, OLE may represent an efficacious adjuvant therapy to normalize glucose homeostasis, prevent and control diabetes and its cardiovascular complications.

Bitter Melon

Bitter melon (BM), also known as *Momordica charantia*, is a popular fruit utilized to treat diabetes and related diseases. A number of preclinical studies have demonstrated the anti-diabetic and hypoglycemic effects of BM via a variety of hypothetical mechanisms. Four clinical trials demonstrated that bitter melon juice, fruit and dry powder have a moderate blood glucose-lowering effect. The compositions of bitter melon extract (BME) seem to be structurally similar to animal insulin. It has been reported that BME can promote glucose uptake, induce insulin release, enhance insulin function, ameliorate obesity-related peripheral inflammation and neuro inflammation, reduce plasma apoB-100/48 in HFD-fed mice, and regulate the phosphorylation of IR, IRS-1 and its downstream signal molecules. In addition, BME stimulates insulin signaling, augments GLUT4 levels, and regulates the content of acylcarnitine in the skeletal muscle of HFD-fed mice. Cucurbitane triterpenoids, a BM bioactive compound, stimulate the translocation of GLUT 4 to cell membrane through activating AMP-activated protein kinase (AMPK) pathway in L6 myotubes and 3T3-L1 adipocytes.

BM supplementation during pregnancy and lactation in rats fed with a high fructose diet alleviates fructose-triggered dyslipidemia and liver oxidative stress in male offspring. BME has been found to maintain normal glucose levels, lipid profiles, and antioxidant status in diabetic rats subjected to a sucrose load. A polyherbal formulation mainly containing BME demonstrates that administration of this extract inverts most blood and tissue alterations caused by STZ-induced diabetes in rats. Methanolic fruit extract of bitter melon also exhibits a dose-dependent hypoglycemic activity in alloxan-induced diabetic albino rats. In addition to increasing insulin sensitivity and lowering blood sugar, BME also has anti-oxidative and cardio-protective properties, which may help to treat diabetic heart fibrosis.

2-Deoxy-D-Glucose (2-DG)

2-deoxy-D-glucose (2-DG), a non-metabolizable glucose analog, is a glycolytic inhibitor and an inhibitor of glucose utilization. 2-DG exists in all kinds of microbes. Its main function is to hinder glycolysis, which induces tumor cell death and protects normal cells. Hence, 2-DG has been extensively investigated as an adjuvant of anti-cancer drugs. The combination of 2-DG and AMPK inhibition has shown synergistically enhanced cytotoxic potential in breast cancer cells with a relative nontoxicity to normal cells and may offer a promising, safe, and effective cancer therapeutic strategy. 2-DG can significantly block glucose uptake by cells. However, no oral administration of 2-DG has been utilized in comparative art.

According to an embodiment of the present disclosure, oral administration of 2-DG is utilized to compete with glucose for the glucose transporters on gastrointestinal cell membrane, and to cause reduction of glucose absorption in the gastrointestinal tract, thus achieving the goal of reducing postprandial blood glucose.

A study utilizing Swiss albino strain 'A' mice administered with 0.2% and 0.4% w/v 2-DG in drinking water for 3 months demonstrates that 2-DG decreases the blood glucose and insulin levels. Another study utilizing rats fed with diet supplemented with 0.4% 2-DG ad libitum on alternating days for 3 and 6 months suggests that 2-DG dietary regimen did indeed exhibit decreases in blood pressure (BP), glucose, and insulin levels, implying an improved gluco-regulation or better glucose homeostasis. A clinical phase I dose-escalation trial of 2-deoxy-D-glucose has identified 63 mg/kg as the clinically tolerable dose. To minimize potential side effects, 800 mg/d 2-DG is utilized in the dietary supplement according to an embodiment of the present disclosure.

Vitamin D

Vitamin D is important for normal calcium and bone homeostasis. Increasing evidence shows that Vitamin D homeostasis is associated with cardiovascular, autoimmune, tumor, lung and neurological diseases. Vitamin D deficiency, or the cognizance of its prevalence, is also increasing. Vitamin D may play a role in the pathogenesis of type 2 diabetes through regulating insulin resistance and/or pancreatic beta cell function. The state of vitamin D or the elements involved in its activation or transport might also be implicated in the development of type 1 diabetes through immunomodulation. In Asian India women with prediabetes, vitamin D levels are relatively low and this is related to higher blood glucose levels. There may be a potential independent role of vitamin D in regulating glucose metabolism in obese patients previously unknown to have abnormal glucose metabolism. Furthermore, vitamin D supplementation may be beneficial to diabetic patients because it improves blood glucose control and diabetic patients with a high 25(OH)D level have better lipid profiles.

Vitamin D may have beneficial effect on fasting glucose in patients with poorly controlled diabetes. Vitamin D treatment in adults with T2DM mellitus may provide a slight decrease in HbA1C, although there are significant heterogeneity between studies. Of note, a recent study focusing on causal or casual association between Vitamin D and diabetes provides recommendation for Vitamin D treatment in diabetes.

Biotin

Biotin may function as a coenzyme in bicarbonate-dependent reactions. It is widely distributed in natural foods even though food composition tables rarely list biotin. Biotin may regulates glucokinase activity, inhibit hepatic glucose output/gluconeogenesis (represses phospoenolpyruvate carboxykinase), and act synergistically with chromium to enhance glucose uptake.

Pilot study and several double-blind randomized clinical trial of Biotin combined with Chromium Picolinate (CrPic) (2 mg biotin/day plus 600 μg CrPic/day for 28-90 days) showed that the combined supplementation decreased HbAlc and fasting plasma glucose (FPG) in patients with T2DM, and improved glucose response following oral glucose tolerance test (OGTT). The combination improved serum lipids in patients with high cholesterol with some effect on TG. Therefore, the combined supplementation may be an effective adjuvant nutritional therapy for those with poorly controlled diabetes with the potential for improving lipid metabolism.

Adverse risk of the biotin-CrPic combination appears to be no different from placebo. However, its long term safety is unknown. Patients with preexisting kidney or liver disease may be more susceptible to adverse effects of chromium. Further, Cr supplementation can interfere with some drugs.

Vitamin C

Vitamin C may function as a hydrophilic anti-oxidant and may regenerate vitamin E, utilized in biosynthesis of collagen, carnitine, and neurotransmitters. Most fruits and vegetables, such as citrus fruits, peppers, tomatoes, potatoes, strawberries, spinach, cruciferous vegetables, contain vitamin C. Vitamin C may improve insulin action, glycemic control, endothelial function, decrease oxidative stress and may be necessary to promote insulin secretion in cultured islet cells.

It's been found that taking vitamin C supplementation at a dosage of 120-1250 mg/day (classically) for 4-16 weeks (or longer, e.g., as long as 9 years) exhibits non-statistical improvement in insulin resistance. The supplementation decreased FPG and tended to reduce HbA1c. Vitamin C supplementation also decreased total cholesterol and LDL levels and tended to improve triglycerides.

High dose vitamin C is commonly considered safe, however, abrupt increases in vitamin C can result in osmotic diarrhea or promote renal excretion. High doses are not recommended for patients with kidney stones, hyperoxaluria, or with impaired renal function Clinical studies show that patients with hyperglycemia have increased demand for vitamin C and high dose Vitamin C supplementation improves glycemic control. Vitamin C may affect oxidative stress and cardiovascular endothelial function. It is prudent to choose a diet rich in fruits/vegetables or supplement Vitamin C for diabetics.

Alpha-Lipoic Acid

Alpha-lipoic acid, or ALA, is a vitamin-like compound and powerful antioxidant. It is known to lower insulin resistance (IR) and help control blood sugar. When people with type 2 diabetes took 300, 600, 900 or 1,200 mg ALA for six months at the same time of routine diabetes treatment, fasting blood glucose and A1C values decreased more as the dose increased. ALA improves insulin sensitivity and cell uptake of blood glucose, although it may take months to experience these effects. It can also prevent oxidative damage caused by hyperglycemia.

The ingredients of the inventive dietary supplement may synergistically work together to improve glycemic control.

As used herein, the standardized extract of *astragalus* root refers to the 4:1 water extract of *astragalus* (10%) including *astragalus* polysaccharide and astragaloside.

As used herein, phlorizin refers to the compound extracted from the root bark of an apple tree.

As used herein, the standardized extract of root bark of white mulberry refers to 4:1 water extract of the mixture of a 10% extract.

As used herein, the standardized extract of olive leaf refers to the mixture of a 10% extract.

As used herein, the standardized extract of bitter melon refers to 4:1 water extract of the mixture of a 50% extract.

Example 1

The composition of an example dietary supplement, i.e., Example Formula 1, according to embodiments of the present disclosure is shown in Table 1 below. In Table 1, the % (w/w) represents the weight percentage of the respective component based on the total weight of all components of Example Formula 1. The daily dose represents an example daily amount (mg) for a patient and the amount in 1 capsule represents an example amount included in a capsule.

TABLE 1

| Components of Example Formula 1 | Daily dose(DD) (mg) | Amount in 1 capsule (mg) | % (w/w) |
|---|---|---|---|
| Standard extract of astragalus root | 250 | 62.5 | 8.01 |
| phlorizin | 450 | 112.5 | 14.41 |
| standardized extract of root bark of white mulberry root | 800 | 200 | 25.62 |
| chromium picolinate (CrPic) | 0.6 | 0.150 | 0.02 |
| standardized extract of olive leaf | 400 | 100 | 12.81 |
| standardized extract of bitter melon | 300 | 75 | 9.61 |
| 2-deoxy-D-glucose | 800 | 200 | 25.62 |
| vitamin D | 0.015 | 0.004 | 0.00 |
| biotin | 2 | 0.5 | 0.06 |
| vitamin C | 120 | 30.000 | 3.84 |
| Total | 3122.615 | 780.65375 | 100.0 |

The dietary supplement of Example 1 can be made into a form for oral administration, such as a tablet, a soft or hard capsule, liquid, a suspension, etc. It is suggested to take 2 doses (e.g., capsules) of the dietary supplement of Example 1 twice per day before meals.

Example 2

The composition of an example dietary supplement, i.e., Example Formula 2, according to embodiments of the present disclosure is shown in Table 2 below.

TABLE 2

| Components of Example Formula 1 | Daily dose(DD) (mg) | Amount in 1 capsule (mg) | % (w/w) |
|---|---|---|---|
| Standard extract of astragalus root | 250 | 62.5 | 8.01 |
| phlorizin | 450 | 112.5 | 14.41 |
| standardized extract of root bark of white mulberry root | 800 | 200 | 25.62 |
| chromium picolinate (CrPic) | 0.6 | 0.150 | 0.02 |
| standardized extract of olive leaf | 400 | 100 | 12.81 |
| standardized extract of bitter melon | 300 | 75 | 9.61 |
| alpha-lipoic acid | 800 | 200 | 25.62 |
| vitamin D | 0.015 | 0.004 | 0.00 |
| biotin | 2 | 0.5 | 0.06 |
| vitamin C | 120 | 30.000 | 3.84 |
| Total | 3122.615 | 780.65375 | 100.0 |

The dietary supplement of Example 2 can be made into a form for oral administration, such as a tablet, a soft or hard capsule, liquid, a suspension, etc. It is suggested to take 2 doses (e.g., capsules) of the dietary supplement of Example 2 twice per day before meals.

In Vivo Efficacy Study
    Materials and Methods
    Sample Preparation
    Standardized extracts of astragalus root, root bark of white mulberry, olive leaf, and bitter melon, phlorizin, and chromium, self-prepared or obtained from various vendors, were utilized in this study. 2-deoxy-D-glucose, ALA, vitamin C, and vitamin D were obtained from Sigma Aldrich Corporation.
    Animal and Study Design
    The inhibitory effect of Example Formula 1 and Example Formula 2 (see Table 1 and Table 2) on postprandial hyperglycemia after carbohydrate loading in Sprague-Dawley (SD) rats was assessed. All animal studies were performed according to the Act on Welfare and Management of Animals law—Act No. 105 of Oct. 1, 1973. Six week-old male SD rats were utilized and fed a solid diet for one week. Rats were housed five per cage in a room with a 12:12 hour light:dark cycle and an ambient temperature of 22-25° C. After 4 groups (n=5) were fasted for one day, 2.0 g/kg of sucrose were gavaged concurrently with Example Formula 1 (200 and 400 mg/kg) (e.g., provided at 200 or 400 mg total weight of Example Formula 1 per 1 Kg of the testing subject or patient) or 5 mg/kg Acarbose. The blood samples were collected from the tail after treatment and blood glucose concentrations were determined at 0, 0.5, 1, and 2 hours by utilizing glucose oxidase method.

Figure 2:
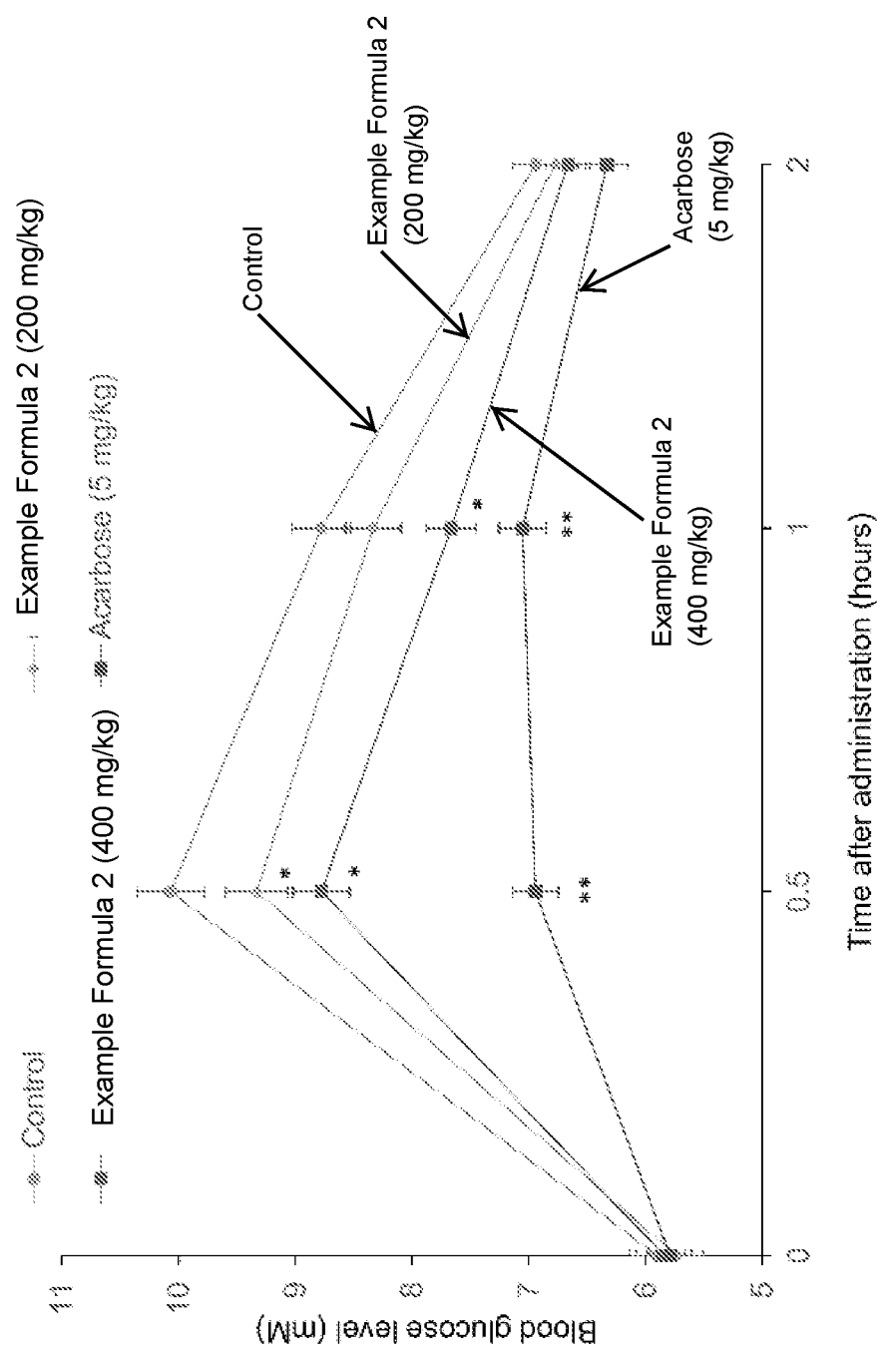
FIG. 2 shows the effect of different dosage of Example Formula 2 on sucrose loading test.

FIG. 1 and FIG. 2 show the effect of different dosage of Example Formula 1 or Example Formula 2 on sucrose loading test. After fasting for one day, 7-week-old, male SD rats were gavaged with sucrose solution (2.0 g/kg) with or without (the Control sample) Example Formula 1 or Example Formula 2. Acarbose was utilized as a positive control. Each point in the drawing represents mean±SD. (n=5). *$p<0.05$, **$p<0.01$ versus their corresponding controls at the same time points by unpaired Student's t-test.

To substantiate the activity of Example Formula 1 or Example Formula 2 in controlling postprandial blood glucose, a sucrose loading test was conducted in SD rat, which is a more relevant animal model for the prevention of type 2 diabetes (T2DM) in normal or pre-diabetic individuals than for the treatment of T2DM. As can be observed from FIGS. 1-2, in SD rats, Example Formula 1 and Example Formula 2 (200 and 400 mg/kg) significantly reduces the blood glucose at 30 minutes after sucrose loading. Example Formula 1 and Example Formula 2 significantly decreases the postprandial hyperglycemia induced by sucrose loading. Though to a lesser extent than those observed in the Acarbose treatment group (the drawing), these data demonstrated the positive effects of Example Formula 1 and Example Formula 2 on post-prandial blood glucose levels caused by high-sucrose meal ingestion. Here, Example Formula 1 and Example Formula 2 have substantially the same effect on reducing the blood glucose.

Comparative Example 1

The composition of Comparative Example Formula 1 is shown in Table 3 below.

TABLE 3

| Components of Comparative Example Formula 1 | Daily dose(DD) (mg) | Amount in 1 capsule (mg) | % (w/w) |
|---|---|---|---|
| Astragalus Root extract | 250 | 125 | 16.0 |
| Phlorizin | 450 | 125 | 16.0 |
| Root bark of white mulberry | 800 | 125 | 16.0 |
| Chromium Picolinate (CrPic) | 0.6 | 0.150 | 0.0 |
| Olive leaf extract | 400 | 125 | 16.0 |
| Bitter Melon Extract | 300 | 125 | 16.0 |
| 2-Deoxy-D-glucose or ALA | 800 | 125 | 16.0 |
| Vitamin D | 0.015 | 0.004 | 0.0 |
| Biotin | 2 | 0.5 | 0.1 |
| Vitamin C | 120 | 30.000 | 3.8 |
| Total | 3122.615 | 780.65375 | 100.0 |

In Vivo Sucrose Loading Test

Figure 3:
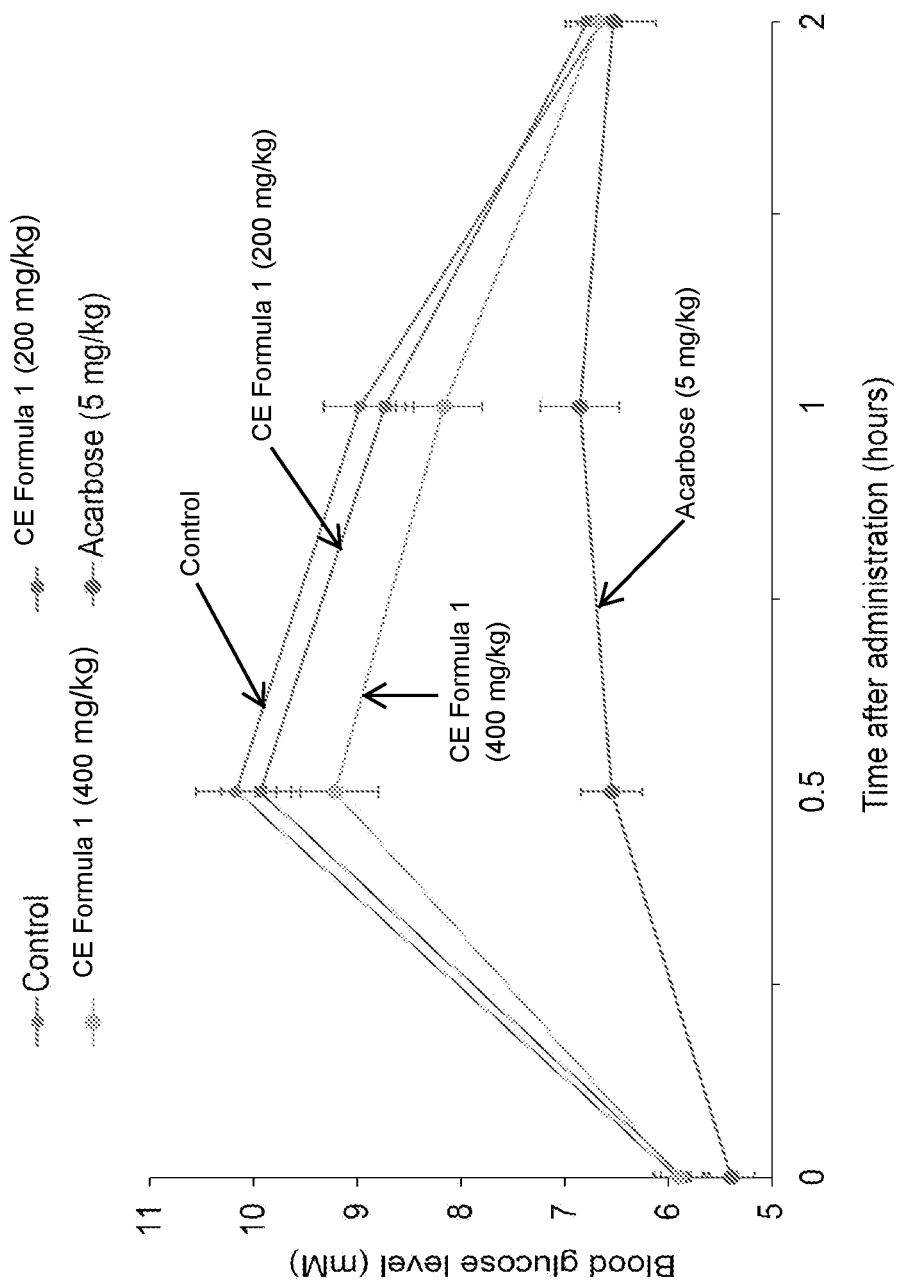
FIG. 3 shows the effect of different dosage of Comparative Example Formula 1 on sucrose loading test.

After fasting for one day, 7-week-old, male SD rats were gavaged with sucrose solution (2.0 g/kg) with or without the Comparative Example Formula 1. Acarbose was used as a positive control. Effect of different dosage of Comparative Example Formula 1 on sucrose loading test is shown in FIG. 3. Each point represents mean±SD. (n=5). *p<0.05, **p<0.01 versus their corresponding controls at the same time points by unpaired Student's t-test.

As shown in FIG. 3, when the same components as Examples 1 and 2 are utilized but at different proportions (e.g., all the important ingredients are formulated with a 1:1 ratio as indicated in Table 3), the effect of reducing postprandial blood sugar level is not as significant as that of Example Formulas 1 and 2.

Table 4 below lists the blood glucose level of rats under different dosage of Example Formula 1 and Comparative Example Formula 1 on sucrose loading test (unit: mM). The procedure is as described above. After fasting for one day, 7-week-old, male SD rats were gavaged with sucrose solution (2.0 g/kg) with or without Example Formula 1 or Comparative Example Formula 1. Acarbose was used as a positive control. Each point represents mean±SD. (n=5). *p<0.05, **p<0.01 versus their corresponding controls at the same time points by unpaired Student's t-test.

TABLE 4

| Time (hour) | 0 | 0.5 | 1 | 2 |
|---|---|---|---|---|
| Control | 5.9 ± 0.2 | 10.2 ± 0.4 | 9.0 ± 0.3 | 6.6 ± 0.2 |
| Example Formula 1 (200 mg/kg) | 5.7 ± 0.2 | 9.3 ± 0.3* | 8.3 ± 0.2 | 6.8 ± 0.2 |
| Comparative Example Formula 1 (200 mg/kg) | 5.8 ± 0.2 | 9.9 ± 0.4 | 8.7 ± 0.3 | 6.8 ± 0.2 |
| Example Formula 1 (400 mg/kg) | 5.8 ± 0.2 | 8.8 ± 0.2* | 7.7 ± 0.2* | 6.7 ± 0.2 |
| Comparative Example Formula 1 (400 mg/kg) | 5.9 ± 0.2 | 9.2 ± 0.4* | 8.2 ± 0.4 | 6.7 ± 0.2 |
| Acarbose (5 mg/kg) | 5.4 ± 0.2 | 6.5 ± 0.3** | 6.9 ± 0.4** | 6.5 ± 0.4 |

The dietary supplement according to embodiments of the present disclosure improves glucose metabolism via augmenting the effects of natural or applied levels of insulin and apposite diet and exercise programs. Through the formulation of the current disclosure, it has been found that dietary supplements including effective amounts of metabolically available forms of chromium and natural vitamin D and C, as well as bioactive components of *astragalus*, phlorizin, white mulberry, olive leaf and bitter melon, can improve glucose metabolism, prevent diabetes, and/or impede the progression of many obesity, diabetes or prediabetes-related diseases, such as cardiovascular complications etc. These components perform diverse functions which, when administered in proper dosages and proportion, synergistically inhibits glucose absorption, promotes glucose metabolism, and/or increases insulin sensitivity, while simultaneously avert or diminish the probability of a cardiovascular event caused by complications associated with obesity, pre-diabetes or diabetes.

The dietary supplement according to embodiments of the present disclosure may be utilized by individuals without obvious diabetic symptoms. However, it is effective for individuals with obesity, impaired glucose tolerance (IGT), pre-diabetes and diabetes to prevent or reduce the need for insulin or other antidiabetic drugs. Furthermore, the dietary supplement contains ingredients that, along with insulin, can also enhance insulin's regulatory role in maintaining homeostasis of blood glucose levels through improving glucose metabolism in insulin-sensitive cells of the body.

The dietary supplement according to embodiments of the present disclosure is not intended to replace other forms of diabetes/IGT treatment, for example, proper diet and exercise, nor does it necessarily exclude the need for insulin.

Given the growing demand for effective non-drug targeting of insulin resistance and development of diabetes, the complementary and alternative nutritional dietary supplement according to embodiments of the present disclosure, without intolerable side effects, may have significant implications for metabolic health and diabetes risk.

Expressions such as "at least one of" or "at least one selected from" when preceding a list of elements, modify the entire list of elements and do not modify the individual elements of the list. Further, the use of "may" when describing embodiments of the present invention refers to "one or more embodiments of the present invention." Also, the term "exemplary" is intended to refer to an example or illustration.

As utilized herein, the term "substantially," "about," and similar terms are utilized as terms of approximation and not as terms of degree, and are intended to account for the inherent deviations in measured or calculated values that would be recognized by those of ordinary skill in the art.

Moreover, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112, first paragraph, or 35 U.S.C. § 112(a), and 35 U.S.C. § 132(a).

As used herein, the term "component" refers to each active ingredient in any of the combinations as disclosed herein for the dietary supplement. For any component specifications that are not disclosed, the component formulation is a standard formulation.

As used herein, the term "standardized extract" refers to a powdered or liquid extract prepared with a measured (e.g., standardized) amount of a major active ingredient or major active ingredients within the herb such that the active ingredients are equal throughout the extract.

As used herein, the term "powder" or "powder extract" refers to a powdered version of a fluid extract or solid extract, in which the powder is made by evaporation methods to remove all liquids. Powder extracts have a concentration ratio of 1:1 or higher.

As used herein, an "excipient" refers to any ingredient other than the disclosed "components" or "active ingredients" of the dietary supplement. The dietary supplement of the present disclosure may be administered alone without an excipient, but may be administered as a formulation in association with one or more acceptable excipients.

Examples of excipients suitable for oral administration include carriers, for example, cellulose, calcium carbonate, dibasic calcium phosphate, mannitol and sodium citrate; granulation binders, for example, polyvinylpyrrolidine, hydroxypropylcellulose (HPC), hydroxypropylmethylcellulose (HPMC) and gelatin; disintegrants, for example, sodium starch glycollate and silicates; lubricating agents, for example, magnesium stearate and stearic acid; wetting agents, for example, sodium lauryl sulphate, preservatives, anti-oxidants, flavours and colourants.

The dietary supplement of the present disclosure may be administered orally in the form a tablet or a capsule. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids or powders, lozenges (including liquid-filled), chews, multi- and nano-particulates, gels, films (including muco-adhesive), ovules, sprays and liquid formulations.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are disclosed in Verma et al, Pharmaceutical Technology On-line, 25(2), 1-14 (2001), the entire content of which is incorporated herein by reference. Other modified release formulations are described in U.S. Pat. No. 6,106,864, the entire content of which is incorporated herein by reference.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

While this invention has been described in detail with particular references to illustrative embodiments thereof, the embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims and equivalents thereof.

What is claimed is:

1. A formulation for a dietary supplement consisting of:
   7.21 to 8.81 wt % of standardized extract of *astragalus* root,
   12.96 to 15.84 wt % of phlorizin,
   23.04 to 28.16 wt % of standardized extract of root bark of white mulberry,
   11.52 to 14.08 wt % of standardized extract of olive leaf,
   8.64 to 10.56 wt % of standardized extract of bitter melon,
   23.04 to 28.16 wt % of at least one selected from 2-Deoxy-D-glucose and alpha-lipoic acid,
   0.09 to 0.11 wt % of biotin,
   3.42 to 4.18 wt % of vitamin C, and
   trace amount of chromium and vitamin D,
   each based on a total weight of the formulation, and
   wherein the dietary supplement is a tablet, a soft capsule or a hard capsule.

2. The formulation of claim 1, wherein the standardized extract of *astragalus* root, phlorizin, standardized extract of root bark of white mulberry, standardized extract of olive leaf, and standardized extract of bitter melon are included at a ratio of 1:1.8:3.2:1.6:1.2.

3. The formulation of claim 1, consisting of 8.01% of standardized extract of *astragalus* root, 14.41% of phlorizin, 25.62% of standardized extract of root bark of white mulberry, 12.81% of standardized extract of olive leaf, 9.61% of standardized extract of bitter melon, 25.62% of alpha-lipoic acid, 0.06% of biotin, 3.84% of vitamin C, and trace amount of chromium picolinate and vitamin D, based on the total weight of the formulation.

4. The formulation of claim 1, wherein the dietary supplement is for oral consumption.

5. A formulation for a dietary supplement consisting of standardized extract of *astragalus* root, phlorizin, standardized extract of root bark of white mulberry, standardized extract of olive leaf, standardized extract of bitter melon, and alpha-lipoic acid, and optional biotin and vitamin C, and
   wherein the dietary supplement is a tablet, a soft capsule or a hard capsule.

6. A method of controlling postprandial blood glucose, the method comprising administering to a patient the formulation for the dietary supplement of claim 5.

7. The formulation of claim 5, wherein the standardized extract of *astragalus* root, phlorizin, standardized extract of root bark of white mulberry, standardized extract of olive leaf, and standardized extract of bitter melon are included at a ratio of 1:1.8:3.2:1.6:1.2.

8. The formulation of claim 5, wherein the optional biotin and vitamin C are both in the formulation.

9. The formulation of claim 8, consisting of 8.01% of standardized extract of *astragalus* root, 14.41% of phlorizin, 25.62% of standardized extract of root bark of white mulberry, 12.81% of standardized extract of olive leaf, 9.61% of standardized extract of bitter melon, 25.62% of alpha-lipoic acid, 0.06% of biotin, and 3.84% of vitamin C.

10. The formulation of claim 5, wherein the dietary supplement is for oral consumption.

11. A method of controlling postprandial blood glucose, the method comprising administering the formulation for the dietary supplement according to claim 5 to a patient.

12. The method of claim 11, wherein the standardized extract of *astragalus* root, phlorizin, standardized extract of root bark of white mulberry, standardized extract of olive leaf, and standardized extract of bitter melon are included at a ratio of 1:1.8:3.2:1.6:1.2.

13. The method of claim 11, wherein the formulation consists of comprising 8.01% of standardized extract of

*astragalus* root, 14.41% of phlorizin, 25.62% of standardized extract of root bark of white mulberry, 12.81% of standardized extract of olive leaf, 9.61% of standardized extract of bitter melon, 25.62% of alpha-lipoic acid, 0.06% of biotin, 3.84% of vitamin C, and trace amount of chromium picolinate and vitamin D, based on a total weight of the formulation.

14. The method of claim 11, wherein the administering is through oral consumption.

15. The method of claim 11, wherein the administering is repeated twice per day before meals, and a total weight of the formulation is about 780 mg.

16. The method of claim 11, wherein the patient has one or more of obesity, impaired glucose tolerance, pre-diabetes and diabetes.

* * * * *